US011446221B2

(12) United States Patent
Yoshida et al.

(10) Patent No.: US 11,446,221 B2
(45) Date of Patent: Sep. 20, 2022

(54) TRIVALENT METAL-DOPED HEXAGONAL PLATE-SHAPED ZINC OXIDE AND METHOD FOR PRODUCING SAME

(71) Applicant: SAKAI CHEMICAL INDUSTRY CO., LTD., Sakai (JP)

(72) Inventors: Ryohei Yoshida, Fukushima (JP); Mitsuo Hashimoto, Fukushima (JP); Kazutaka Murai, Fukushima (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 343 days.

(21) Appl. No.: 16/620,800

(22) PCT Filed: Jun. 8, 2018

(86) PCT No.: PCT/JP2018/022075
§ 371 (c)(1),
(2) Date: Dec. 9, 2019

(87) PCT Pub. No.: WO2018/230473
PCT Pub. Date: Dec. 20, 2018

(65) Prior Publication Data
US 2020/0129394 A1      Apr. 30, 2020

(30) Foreign Application Priority Data

Jun. 12, 2017   (JP) ............................. JP2017-115410

(51) Int. Cl.
*B32B 5/16*      (2006.01)
*A61K 8/27*      (2006.01)
(Continued)

(52) U.S. Cl.
CPC ............... *A61K 8/27* (2013.01); *A61Q 17/04* (2013.01); *C01G 9/02* (2013.01); *C01P 2002/54* (2013.01);
(Continued)

(58) Field of Classification Search
CPC .. C09C 1/043; C09C 2210/10; C01P 2004/80; C01P 2004/84; Y10T 428/2991
(Continued)

(56) References Cited

U.S. PATENT DOCUMENTS 5,102,650 A      4/1992  Hayashi et al.
2006/0073092 A1*  4/2006  Katusic .................. B82Y 30/00
                                                           423/622
(Continued)

FOREIGN PATENT DOCUMENTS

CN           102395532       3/2012
EP           1 527 017       11/2010
(Continued)

OTHER PUBLICATIONS

Alkahlout et al., Synthesis and Characterization of Aluminum Doped Zinc Oxide Nanostructures via Hydrothermal Route, Journal of Materials, vol. 2014, Article ID 235638, 8 pages http://dx.doi.org/10.1155/2014/235638 (Year: 2014).*
(Continued)

*Primary Examiner* — Hoa (Holly) Le
(74) *Attorney, Agent, or Firm* — Hamre, Schumann, Mueller & Larson, P.C.

(57) ABSTRACT

The present invention provides zinc oxide having excellent infrared blocking ability, high whiteness, and excellent texture during use. The present invention relates to trivalent metal-doped hexagonal plate-shaped zinc oxide having an aspect ratio of 2.5 or greater, the trivalent metal-doped hexagonal plate-shaped zinc oxide having a trivalent metal element content based on the zinc element of 0.15 to 5 mol %, a whiteness of 90 or higher, and a powder spectral reflectance at a wavelength of 1500 nm of 80% or less.

7 Claims, 3 Drawing Sheets

Example 1 ( × 20000)

Example 1 ( × 10000)

(51) Int. Cl.
*A61Q 17/04* (2006.01)
*C01G 9/02* (2006.01)

(52) U.S. Cl.
CPC ...... *C01P 2002/72* (2013.01); *C01P 2004/01* (2013.01); *C01P 2004/24* (2013.01); *C01P 2004/54* (2013.01); *C01P 2004/61* (2013.01); *C01P 2004/62* (2013.01); *C01P 2006/60* (2013.01)

(58) Field of Classification Search
USPC .......................................................... 428/403
See application file for complete search history.

(56) References Cited

U.S. PATENT DOCUMENTS

| | | | |
|---|---|---|---|
| 2010/0047590 A1* | 2/2010 | Ueda | B32B 17/06 428/432 |
| 2012/0097888 A1 | 4/2012 | Takabatake | |
| 2014/0050925 A1 | 2/2014 | Sueda et al. | |
| 2014/0112862 A1 | 4/2014 | Sueda et al. | |
| 2016/0319131 A1 | 11/2016 | Sueda et al. | |
| 2016/0324742 A1 | 11/2016 | Sueda et al. | |
| 2016/0347624 A1 | 12/2016 | Yoshida et al. | |

FOREIGN PATENT DOCUMENTS

| | | |
|---|---|---|
| JP | 4-026514 | 1/1992 |
| JP | 6-072821 | 3/1994 |
| JP | 6-080421 | 3/1994 |
| JP | 7-069627 | 3/1995 |
| JP | 2003-054947 | 2/2003 |
| JP | 2016-013953 | 1/2016 |
| WO | 2004/014800 | 2/2004 |
| WO | 2012/147886 | 11/2012 |
| WO | 2015/033990 | 3/2015 |
| WO | 2015/098992 | 7/2015 |
| WO | 2015098945 | 7/2015 |
| WO | 2015/118777 | 8/2015 |

OTHER PUBLICATIONS

Xu, et al., "Controllable morphology evolution of electrodeposited ZnO nano/micro-scale structures in aqueous solution", Materials and Design 30 (2009) 1704-1711.

Pal, et al., Influence of Al doping on microstructual, optical an photocatalytic properties of sol-gel based nanostructured zinc oxide films on glass, RSC Advances, vol. 4, 2014, pp. 11552-11563.

* cited by examiner

Example 1 (×20000)

Example 1 (×10000)

Example 3 (×20000)

Example 3 (×10000)

Example 4 (×20000)

Example 4 (×10000)

Comparative Example 1 (×20000)

Comparative Example 1 (×10000)

Comparative Example 3 (×20000)

Comparative Example 3 (×10000)

Comparative Example 4 (×20000)

Comparative Example 4 (×10000)

Comparative Example 5 (×20000)

Comparative Example 5 (×10000)

TRIVALENT METAL-DOPED HEXAGONAL PLATE-SHAPED ZINC OXIDE AND METHOD FOR PRODUCING SAME

TECHNICAL FIELD

The present invention relates to trivalent metal-doped hexagonal plate-shaped zinc oxide and methods for producing the trivalent metal-doped hexagonal plate-shaped zinc oxide. Specifically, the present invention relates to trivalent metal-doped hexagonal plate-shaped zinc oxide suitable for applications such as cosmetics and a method for producing the trivalent metal-doped hexagonal plate-shaped zinc oxide.

BACKGROUND ART

In recent years, more and more cosmetics have contained components for protecting skin from infrared light in sunlight or other light, and various components capable of absorbing or reflecting infrared light have been used. For example, zinc oxide is used. Particulate hexagonal plate-shaped zinc oxide is more capable of reflecting infrared light than amorphous particulate zinc oxide, and is used as a cosmetic component (see Patent Literatures 1 and 2). Although such a conventional hexagonal plate-shaped zinc oxide can reflect infrared light, it has a low infrared light absorption and thus insufficiently blocks infrared light.

Meanwhile, there have been attempts to dope zinc oxide with an additional element to impart conductivity or to enhance the ability to block light such as infrared light. It has been reported that aluminum-doped zinc oxide has excellent conductivity and excellent ability to block light such as infrared light (see Patent Literatures 3 to 7).

CITATION LIST

Patent Literature

Patent Literature 1: WO 2012/147886
Patent Literature 2: WO 2015/118777
Patent Literature 3: JP H04-26514 A
Patent Literature 4: JP 2003-54947 A
Patent Literature 5: JP 2016-13953 A
Patent Literature 6: JP H06-80421 A
Patent Literature 7: JP H07-69627 A

SUMMARY OF INVENTION

Technical Problem

Although aluminum-doped zinc oxide has been proposed as a material having excellent infrared blocking ability as described above, such conventional aluminum-doped zinc oxide is gray or blue-white when it is in the form of powder, and thus needs to be subjected to color adjustment. Accordingly, conventional one is limited in applications. Aluminum-doped zinc oxide suitable for products in which color is important, such as cosmetics, needs to have high whiteness when it is in the form of powder. Also, aluminum-doped zinc oxide suitable for cosmetics needs to have good texture during use. Conventional aluminum-doped zinc oxide insufficiently satisfies these properties. Thus, zinc oxide excellent in infrared blocking ability and these properties has been demanded.

The present invention has been made in view of the state of the art and aims to provide zinc oxide having excellent infrared blocking ability, high whiteness, and excellent texture during use.

Solution to Problem

The present inventors examined a method for producing zinc oxide having excellent infrared blocking ability, high whiteness, and excellent texture during use and found that trivalent metal-doped zinc oxide having excellent infrared absorbing ability can be obtained by a method including preparing a slurry mixture containing starting particulate zinc oxide, a zinc acetate solution, and a trivalent metal chloride as a metal source and heat aging the resulting slurry mixture at 60° C. to 100° C. This method provides trivalent metal-doped hexagonal plate-shaped zinc oxide having excellent infrared blocking ability, high whiteness, and excellent texture during use. Thereby, the present invention has been completed.

That is, one aspect of the present invention relates to trivalent metal-doped hexagonal plate-shaped zinc oxide, having an aspect ratio of 2.5 or greater, the trivalent metal-doped hexagonal plate-shaped zinc oxide having a trivalent metal element content based on a zinc element of 0.15 to 5 mol %, a whiteness of 90 or higher, and a powder spectral reflectance at a wavelength of 1500 nm of 80% or less.

The trivalent metal is preferably at least one selected from the group consisting of aluminum, gallium, and indium.

The trivalent metal-doped hexagonal plate-shaped zinc oxide preferably has a median size of 0.05 to 5 μm.

The trivalent metal-doped hexagonal plate-shaped zinc oxide preferably has a ratio D90/D10 of 2.5 or less.

Another aspect of the present invention relates to a method for producing trivalent metal-doped hexagonal plate-shaped zinc oxide, the method including:

a step (1) of preparing a slurry mixture containing starting particulate zinc oxide, a zinc acetate solution, and a trivalent metal chloride; and a step (2) of heat aging the slurry mixture obtained in the step (1) at 60° C. to 100° C.

The trivalent metal chloride is preferably used in an amount calculated as trivalent metal element of 0.15 to 5 mol % based on the starting particulate zinc oxide.

The trivalent metal is preferably at least one selected from the group consisting of aluminum, gallium, and indium.

The step (1) further includes adding the trivalent metal chloride to the zinc acetate solution.

The method preferably further includes a step (3) of washing solids obtained from the slurry mixture after the step (2) with water having a temperature from 70° C. to below 100° C.

Advantageous Effects of Invention

The trivalent metal-doped hexagonal plate-shaped zinc oxide of the present invention has excellent infrared blocking ability, high whiteness when it is in the form of powder, and good texture during use, and is thus suitable for cosmetics and many other applications.

DESCRIPTION OF EMBODIMENTS

Figure 1:
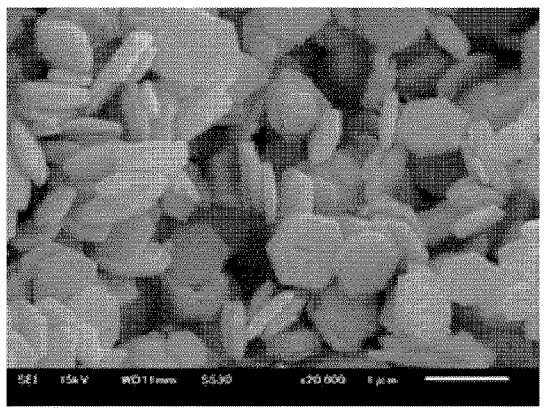
FIG. 1 shows an electron micrograph of particulate aluminum-doped hexagonal plate-shaped zinc oxide obtained in Example 1.
Figure 1:
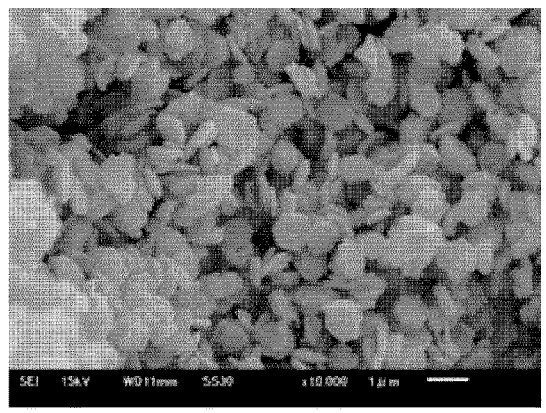

The following description is offered to specifically describe an embodiment of the present invention. It should be noted that the present invention is not limited only to the following description, and the embodiment can be appropriately modified within the scope of the present invention.
<Trivalent Metal-Doped Hexagonal Plate-Shaped Zinc Oxide>

The trivalent metal-doped hexagonal plate-shaped zinc oxide of the present invention has an aspect ratio of 2.5 or greater, a trivalent metal element content based on the zinc element of 0.15 to 5 mol %, a whiteness of 90 or higher, and a powder spectral reflectance at a wavelength of 1500 nm of 80% or less.

Owing to the plate shape having an aspect ratio of 2.5 or greater, the trivalent metal-doped hexagonal plate-shaped zinc oxide has excellent slippage and texture derived from its shape. The aspect ratio of the trivalent metal-doped hexagonal plate-shaped zinc oxide is preferably 2.7 or greater, more preferably 3.0 or greater, still more preferably 4.0 or greater, particularly preferably 4.5 or greater, most preferably 5.0 or greater. The upper value of the aspect ratio is not limited. It is usually 100 or less.

The trivalent metal-doped hexagonal plate-shaped zinc oxide has a trivalent metal element content based on the zinc element of 0.15 to 5 mol %. With such a trivalent metal element content, the effect of doping with the trivalent metal is sufficiently achieved, and a material having excellent infrared blocking ability is obtained. The trivalent metal element content based on the zinc element is more preferably 0.15 to 2 mol %.

The trivalent metal-doped hexagonal plate-shaped zinc oxide of the present invention has a whiteness of 90 or higher. The trivalent metal-doped hexagonal plate-shaped zinc oxide having a high whiteness is suitable for materials for products in which color is important, such as cosmetics. The whiteness is more preferably 92 or higher.

The trivalent metal-doped hexagonal plate-shaped zinc oxide of the present invention has a powder spectral reflectance at a wavelength of 1500 nm of 80% or less. Conventional hexagonal plate-shaped zinc oxide reflects or absorbs infrared light to block it. The trivalent metal-doped hexagonal plate-shaped zinc oxide of the present invention has higher infrared absorbing ability than conventional hexagonal plate-shaped zinc oxide, and thus exhibits better infrared blocking ability. Accordingly, the trivalent metal-doped hexagonal plate-shaped zinc oxide of the present invention has lower reflectance of light having a wavelength of 1500 nm (infrared region) (=higher absorption of light having a wavelength of 1500 nm) than conventional hexagonal plate-shaped zinc oxide.

The powder spectral reflectance at a wavelength of 1500 nm is preferably 76% or less.

The lower value of the powder spectral reflectance at a wavelength of 1500 nm is not limited. It is usually 10% or more.

The trivalent metal-doped hexagonal plate-shaped zinc oxide of the present invention preferably has a brightness L value of 90 or more. The L value is more preferably 92 or more.

The trivalent metal-doped hexagonal plate-shaped zinc oxide of the present invention preferably has a redness a value of −2.5 to 2.5, more preferably −2.0 to 2.0.

The trivalent metal-doped hexagonal plate-shaped zinc oxide of the present invention preferably has a yellowness b value of −2.5 to 2.5.

The trivalent metal-doped hexagonal plate-shaped zinc oxide of the present invention having a brightness L value, a redness a value, and a yellowness b value within the above respective ranges is more suitable for materials for products in which color is important, such as cosmetics.

The trivalent metal-doped hexagonal plate-shaped zinc oxide of the present invention preferably has a median diameter of 0.05 to 5 μm. The trivalent metal-doped hexagonal plate-shaped zinc oxide having such a median diameter exerts an excellent effect of blocking infrared light. The median diameter of the trivalent metal-doped hexagonal plate-shaped zinc oxide is more preferably 0.07 to 4 μm, still more preferably 0.08 to 3.5 μm. The median diameter herein is a particle size at which 50% by number of particles are accumulated (D50) and is determined by the method described in EXAMPLES.

The ratio D90/D10 of the trivalent metal-doped hexagonal plate-shaped zinc oxide of the present invention is preferably 2.5 or less. With such a narrow particle size distribution, variation in quality is reduced, and thus desired properties can be more sufficiently achieved. The ratio D90/D10 of the trivalent metal-doped hexagonal plate-shaped zinc oxide is more preferably 2.3 or less, still more preferably 2.2 or less.

The aspect ratio, the trivalent metal element content based on the zinc element, the whiteness, the powder spectral reflectance at a wavelength of 1500 nm, the brightness L value, the redness a value, the yellowness b value, and the median size of the trivalent metal-doped hexagonal plate-shaped zinc oxide of the present invention can be determined by the methods described in EXAMPLES.

Examples of the trivalent metal element in the trivalent metal-doped hexagonal plate-shaped zinc oxide of the present invention include aluminum, gallium, and indium. One or more of these may be present. Preferred among these trivalent metals is aluminum or gallium, with aluminum being more preferred, because they are inexpensive.

The trivalent metal-doped hexagonal plate-shaped zinc oxide of the present invention may be subjected to surface treatment as needed. Non-limiting examples of the surface treatment include inorganic surface treatments for forming an inorganic oxide layer such as a silica layer, an alumina layer, a zirconia layer, or a titania layer and organic surface treatments using an organic silicon compound, an organic aluminum compound, an organic titanium compound, a higher fatty acid, a metal soap, a polyol, or an alkanolamine. The trivalent metal-doped hexagonal plate-shaped zinc oxide may be subjected to two or more surface treatments.

Since the trivalent metal-doped hexagonal plate-shaped zinc oxide of the present invention has excellent infrared blocking ability, high whiteness when it is in the form of powder, and good texture during use, it is suitable for materials for cosmetics. The trivalent metal-doped hexagonal plate-shaped zinc oxide of the present invention suitable for cosmetics can be obviously used in industrial applications such as resin compositions and coating materials.

<Method for Producing Trivalent Metal-Doped Hexagonal Plate-Shaped Zinc Oxide>

The method for producing trivalent metal-doped hexagonal plate-shaped zinc oxide of the present invention includes a step (1) of preparing a slurry mixture containing starting particulate zinc oxide, a zinc acetate solution, and a trivalent metal chloride and a step (2) of heat aging the slurry mixture obtained in the step (1) at 60° C. to 100° C.

In the step (1), the starting particulate zinc oxide, the zinc acetate solution, and the trivalent metal chloride may be mixed in any order as long as the slurry containing these is prepared. Specifically, the starting particulate zinc oxide may first be mixed with the zinc acetate solution, followed by mixing with the trivalent metal chloride; or the starting particulate zinc oxide or zinc acetate solution may first be mixed with the trivalent metal chloride, followed by mixing with the rest; or these three components may be simultaneously mixed.

In the mixing, to the starting particulate zinc oxide, the zinc acetate solution, or the trivalent metal chloride may be added the others, or two or three of the components may be added to a solvent.

In the mixing, each component may be added in one portion or several portions.

The step (1) preferably further includes adding the trivalent metal chloride to the zinc acetate solution. The step in which the trivalent metal chloride is added to the zinc acetate solution in advance, and the resulting solution is mixed with the starting particulate zinc oxide presumably allows growth of more uniform crystals, leading to trivalent metal-doped hexagonal plate-shaped zinc oxide having higher infrared blocking ability.

In the step (1), the starting particulate zinc oxide, the zinc acetate solution, and the trivalent metal chloride are preferably mixed by stirring to prepare the slurry mixture. The stirring may be performed by any method.

In the step (1), the starting particulate zinc oxide and the trivalent metal chloride each may be subjected to mixing in the form of powder, slurry, or solution. In order to obtain trivalent metal-doped hexagonal plate-shaped zinc oxide having a narrow particle size distribution, each of them is preferably subjected to mixing in the form of slurry or solution.

The slurry and the solution are preferably prepared using water as a solvent.

When the mixing is performed by adding any two or three of the starting particulate zinc oxide, the zinc acetate solution, and the trivalent metal chloride to a solvent, the solvent is preferably water.

When the starting particulate zinc oxide and the trivalent metal chloride are each subjected to mixing in the form of slurry or solution, any amount of a solvent may be used. The amount of the solvent is preferably 1 to 500 ml, more preferably 5 to 100 ml per gram of the starting particulate zinc oxide or trivalent metal chloride.

The zinc acetate solution in the step (1) may contain any solvent as long as zinc acetate is present in solution. The solvent is preferably water. That is, the zinc acetate solution in the step (1) is preferably an aqueous solution of zinc acetate.

The concentration of the zinc acetate solution in the step (1) is preferably 0.1 to 4 mol/l, more preferably 0.3 to 3 mol/l, still more preferably 0.5 to 2 mol/l.

The starting particulate zinc oxide used in the step (1) preferably has a particle size calculated from specific surface area of 0.001 to 1 μm. The starting particulate zinc oxide having such a particle size can lead to trivalent metal-doped hexagonal plate-shaped zinc oxide having much better infrared blocking ability, which is suitable for applications such as cosmetics. The particle size of the starting particulate zinc oxide is more preferably 0.002 to 0.1 μm.

The particle size calculated from specific surface area of the starting particulate zinc oxide corresponds to the diameter of a sphere in which the surface area is equal to the specific surface area determined by the BET method. Specifically, the particle size is a value determined using the following equation:

Particle size calculated from specific surface area of starting particulate zinc oxide (μm)=$[6/(Sg \times \rho)]$ (Sg ($m^2$/g): specific surface area, ρ (g/$cm^3$): absolute gravity of particle), where Sg is a specific surface area determined with a fully automatic BET specific surface area measuring apparatus Macsorb Model HM-1200 (Mountech Co., Ltd.) and ρ is the absolute gravity of zinc oxide.

The absolute gravity p of particle in the calculation is 5.6 which is the absolute gravity of zinc oxide.

In the step (1), the amount of the zinc acetate solution used to prepare the slurry mixture containing starting particulate zinc oxide, a zinc acetate solution, and a trivalent metal chloride is preferably such that the amount of the zinc acetate in the zinc acetate solution is 0.1 to 3 mol per mole of the starting particulate zinc oxide. Use of the zinc acetate solution in an amount satisfying such a ratio leads to uniform hexagonal particles. The amount of the zinc acetate solution is more preferably such that the amount of the zinc acetate therein is 0.2 to 1 mol.

In the step (1), the trivalent metal chloride is preferably used in an amount calculated as trivalent metal element of 0.15 to 5 mol % based on the starting particulate zinc oxide. Use of the trivalent metal chloride at such a ratio allows doping of zinc oxide with a more sufficient amount of trivalent metal. The trivalent metal chloride is more preferably used in an amount calculated as trivalent metal element of 0.15 to 3 mol % based on the starting particulate zinc oxide.

Examples of the trivalent metal chloride used in the step (1) include chlorides of aluminum, gallium, and indium. One or more of these chlorides may be present in the trivalent metal-doped hexagonal plate-shaped zinc oxide of the present invention. Preferred among these trivalent metals is aluminum or gallium, with aluminum being more preferred, because they are inexpensive.

The concentration of the zinc acetate in the slurry mixture containing starting particulate zinc oxide, a zinc acetate solution, and a trivalent metal chloride prepared in the step (1) is preferably 0.1 to 3 mol/l, more preferably 0.2 to 1 mol/l.

In the step (1), the slurry containing starting particulate zinc oxide, a zinc acetate solution, and a trivalent metal chloride may be mixed at any temperature. The temperature is preferably 3° C. to 50° C., more preferably 10° C. to 40° C.

In the step (1), the slurry containing starting particulate zinc oxide, a zinc acetate solution, and a trivalent metal chloride may be mixed for any length of time. The length of time may be appropriately set depending on the amounts of the starting materials, and is preferably 1 to 480 minutes, more preferably 30 to 360 minutes.

When the trivalent metal chloride is added to the zinc acetate solution in advance, and the resulting solution is mixed with the starting particulate zinc oxide in the step (1), the length of time to mix the zinc acetate solution containing the trivalent metal chloride with the starting particulate zinc oxide may preferably be, but not limited to, 10 to 420 minutes, more preferably 30 to 300 minutes.

The step (2) is a step of heat aging the slurry mixture obtained in the step (1) at 60° C. to 100° C. The heat aging allows production of uniformly hexagonal plate-shaped particles. The temperature of heating may be 60° C. to 100° C., preferably 70° C. to 100° C., more preferably 80° C. to 100° C., still more preferably 90° C. to 100° C. The slurry mixture may be heat aged under stirring or by allowing it to stand. It is preferably heat aged under stirring.

The heat aging in the step (2) may be performed for any length of time. In view of the yield and productivity of the trivalent metal-doped hexagonal plate-shaped zinc oxide, the length of time is preferably 10 to 540 minutes, more preferably 20 to 420 minutes, still more preferably 30 to 300 minutes.

In the heat aging, the slurry mixture obtained in the step (1) is preferably heated to 60° C. to 100° C. at a temperature rise rate of 10° C./min or less. Such a temperature rise rate allows enough time to grow crystals and thus can lead to uniform trivalent metal-doped hexagonal plate-shaped zinc oxide having a small variation in particle size. The temperature rise rate is more preferably 5° C./min or less, still more preferably 3° C./min or less.

The method for producing trivalent metal-doped hexagonal plate-shaped zinc oxide of the present invention preferably further includes a step (3) of washing solids obtained from the slurry mixture after the step (2) with water having a temperature from 70° C. to below 100° C. The step (3) can be performed by stirring the solids (cake) obtained by filtering the slurry mixture obtained in the step (2) in water having a temperature from 70° C. to below 100° C. This step allows more sufficient removal of excess salts such as unreacted zinc acetate and thus can lead to uniform trivalent metal-doped hexagonal plate-shaped zinc oxide having a small variation in particle size.

The temperature in the step (3) should range from 70° C. to below 100° C., preferably from 80° C. to below 100° C., more preferably from 90° C. to below 100° C.

The method for producing trivalent metal-doped hexagonal plate-shaped zinc oxide of the present invention may further include filtering and/or washing (with water) after the step (2) (between the steps (2) and (3)) or after the step (3). This step(s) allows removal of excess salts such as unreacted starting materials and thus can lead to high purity trivalent metal-doped hexagonal plate-shaped zinc oxide. The method may further include cooling the liquid before filtering.

The amount of water used for washing after the step (2), after the step (3), or during the step (3) is preferably 1000% by mass or more relative to 100% by mass of the solids to be washed. Such an amount of water allows more sufficient removal of excess salts in the solids.

The length of time of the step (3) may be appropriately set depending on the amounts of the solids and water to be used, and is preferably 10 to 540 minutes, more preferably 30 to 480 minutes.

The method for producing trivalent metal-doped hexagonal plate-shaped zinc oxide of the present invention may further include drying the trivalent metal-doped hexagonal plate-shaped zinc oxide.

The trivalent metal-doped hexagonal plate-shaped zinc oxide may be dried at any temperature as long as the trivalent metal-doped hexagonal plate-shaped zinc oxide is dried. The temperature is preferably 100° C. to 200° C., more preferably 110° C. to 150° C.

The trivalent metal-doped hexagonal plate-shaped zinc oxide may be dried for any length of time. The length of time is preferably 6 to 200 hours, more preferably 12 to 170 hours.

The method for producing trivalent metal-doped hexagonal plate-shaped zinc oxide of the present invention may further include additional steps other than the steps (1) to (3), washing, filtering, and drying steps. The additional steps include an optional surface treatment step. The additional steps may be performed before or after any of the steps (1) to (3).

In the method for producing trivalent metal-doped hexagonal plate-shaped zinc oxide of the present invention, each of the steps (1) to (3), washing, filtering, drying, and additional steps may be performed one or more times.

EXAMPLES

Hereinafter, the present invention will be described with reference to examples. However, the present invention is not limited to these examples. The terms "%" and "part(s)" represent "% by mass (% by weight)" and "part(s) by mass (part(s) by weight)", respectively, unless otherwise specified.

Example 1

Figure 2:
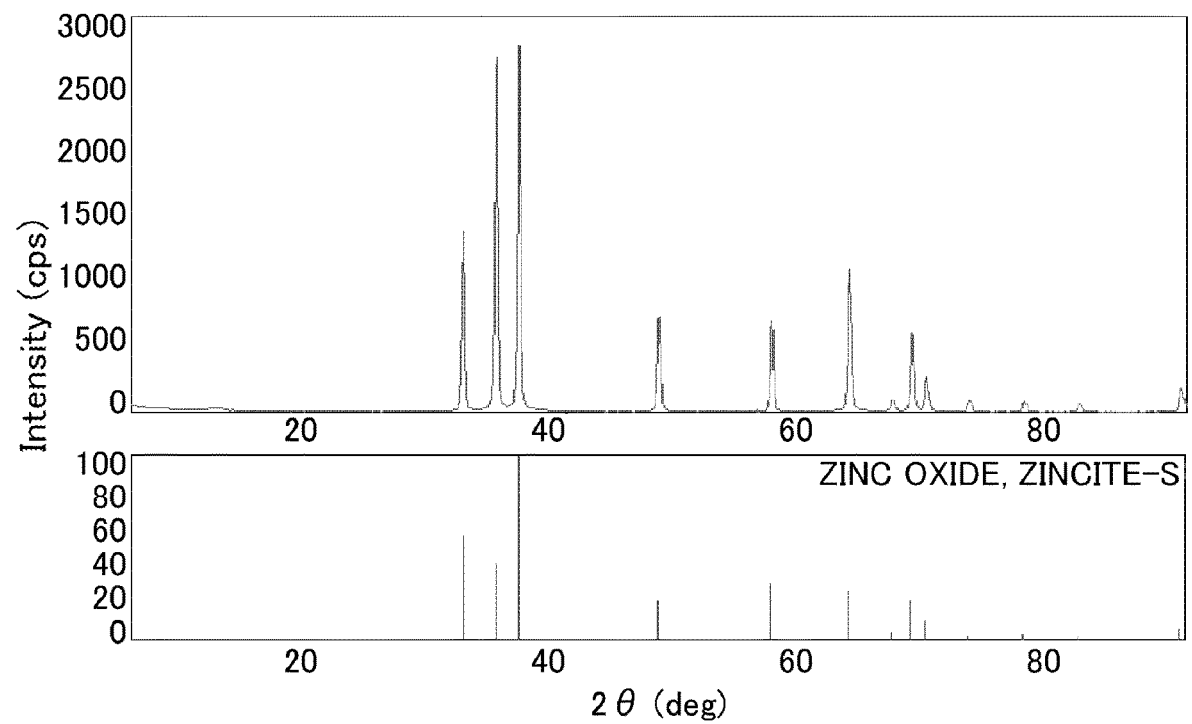
FIG. 2 shows an X-ray diffraction spectrum of the particulate aluminum-doped hexagonal plate-shaped zinc oxide obtained by analysis with an X-ray diffractometer Ultima III (Rigaku Corporation) in Example 1.
Figure 3:
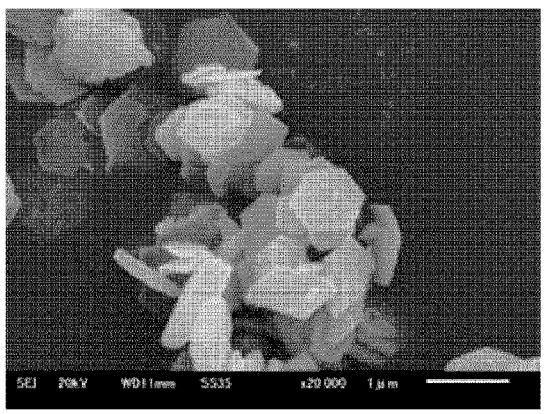
FIG. 3 shows an electron micrograph of particulate aluminum-doped hexagonal plate-shaped zinc oxide obtained in Example 3.
Figure 3:
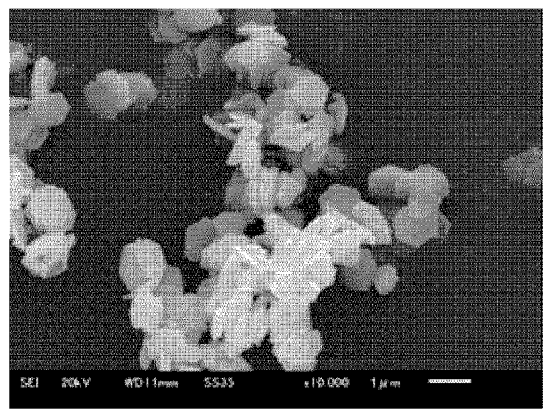
Figure 4:
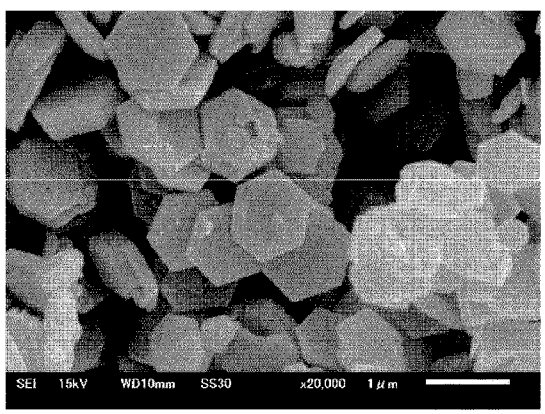
FIG. 4 shows an electron micrograph of particulate aluminum-doped hexagonal plate-shaped zinc oxide obtained in Example 4
Figure 4:
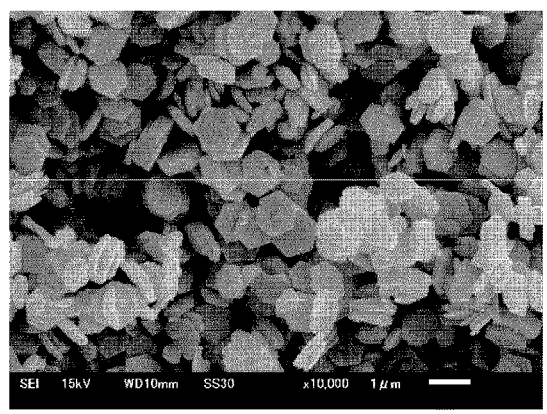
Figure 5:
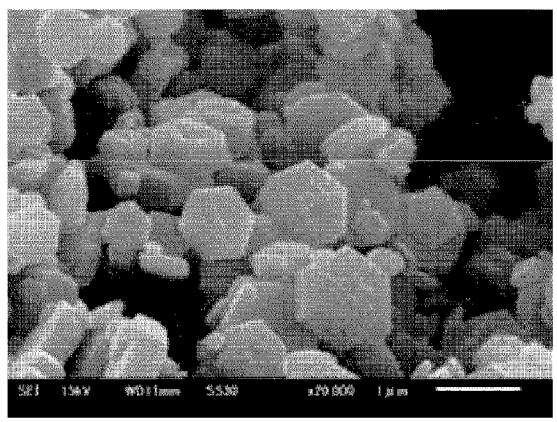
FIG. 5 shows an electron micrograph of particulate hexagonal plate-shaped zinc oxide obtained in Comparative Example 1
Figure 5:
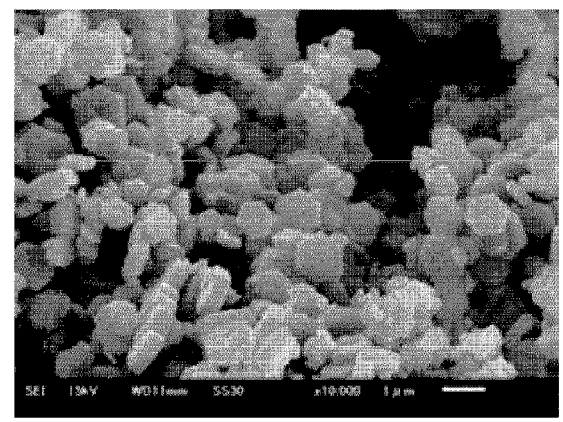
Figure 6:
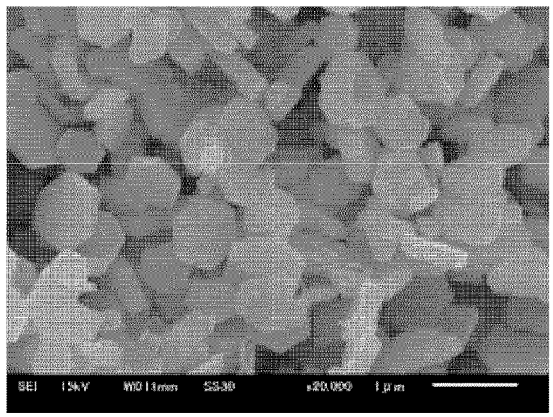
FIG. 6 shows an electron micrograph of particulate aluminum-doped hexagonal plate-shaped zinc oxide obtained in Comparative Example 3.
Figure 6:
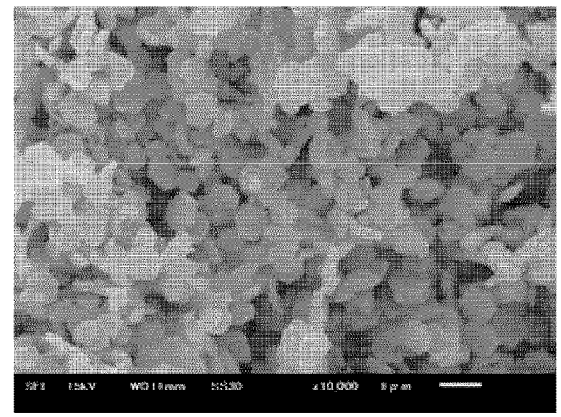
Figure 7:
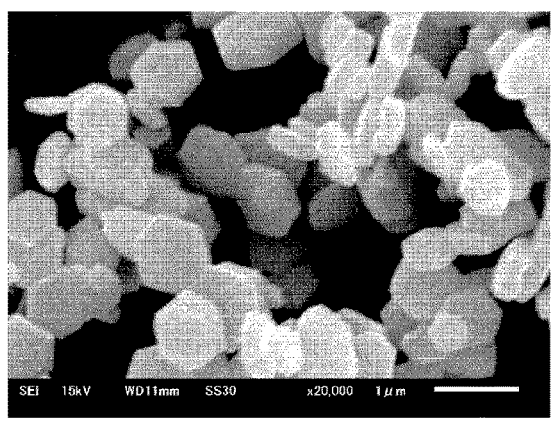
FIG. 7 shows an electron micrograph of particulate aluminum-doped hexagonal plate-shaped zinc oxide obtained in Comparative Example 4.
Figure 7:
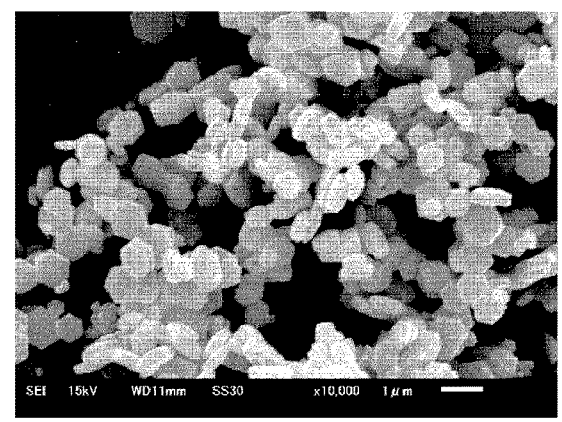
Figure 8:
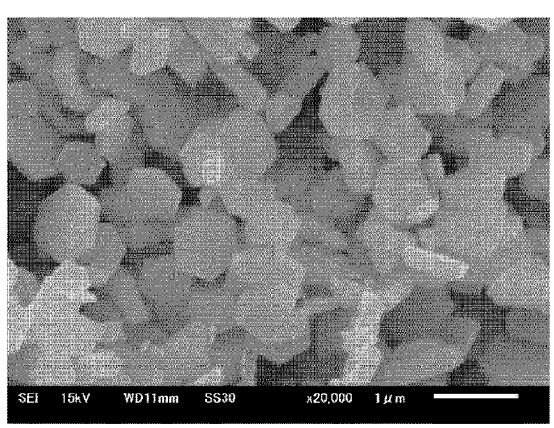
FIG. 8 shows an electron micrograph of particulate aluminum-doped hexagonal plate-shaped zinc oxide obtained in Comparative Example 5.
Figure 8:
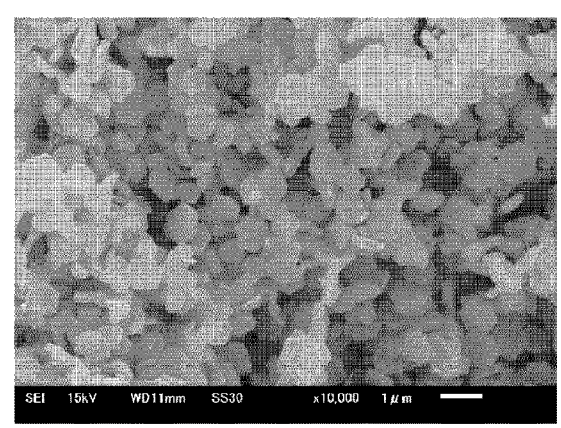

A slurry was obtained by repulping 79.2 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 2.37 g of aluminum chloride hexahydrate (Al element: 1 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Al-doped hexagonal plate-shaped zinc oxide was obtained. The size and shape of the resulting particles were observed with a scanning electron microscope JSM-6510A (JEOL Ltd.). The resulting electron micrographs are shown in FIG. 1. The particles were analyzed with an X-ray diffractometer Ultima III (Rigaku Corporation). The resulting X-ray diffraction spectrum is shown in FIG. 2. The properties of the particles were evaluated. The results are shown in Table 1.

Example 2

A slurry was obtained by repulping 79.6 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 1.19 g of aluminum chloride hexahydrate (Al element: 0.5 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Al-doped hexagonal plate-shaped zinc oxide was obtained.

Example 3

A slurry was obtained by repulping 78.4 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 4.75 g of aluminum chloride hexahydrate (Al element: 2 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Al-doped hexagonal plate-shaped zinc oxide was obtained.

Example 4

A slurry was obtained by repulping 79.2 g of starting particulate zinc oxide (FINEX-50 available from Sakai Chemical Industry Co., Ltd., particle size calculated from specific surface area: 0.02 μm) with 399 ml of water. To the slurry was added 2.37 g of aluminum chloride hexahydrate (Al element: 1 mol % based on the starting particulate zinc oxide). Separately, 601 ml of a 1.30 mol/l aqueous solution of zinc acetate was prepared. The zinc acetate aqueous solution and the slurry containing the starting particulate zinc oxide and aluminum chloride were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Al-doped hexagonal plate-shaped zinc oxide was obtained.

Example 5

A slurry was obtained by repulping 80.0 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 5.19 g of gallium chloride (Ga element: 3 mol % based on the starting particulate zinc oxide). The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the gallium chloride was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Ga-doped hexagonal plate-shaped zinc oxide was obtained.

Comparative Example 1

A slurry was obtained by repulping 80 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. The slurry of the starting particulate zinc oxide and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate and the starting particulate zinc oxide was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate hexagonal plate-shaped zinc oxide was obtained.

Comparative Example 2

The properties of commercially available conductive zinc oxide ("23-K" available from Hakusui Tech Co., Ltd.) were measured.

Comparative Example 3

A slurry was obtained by repulping 79.2 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 3.30 g of aluminum sulfate so that the amount of aluminum was 1 mol % based on the starting zinc oxide. The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and the aluminum sulfate was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Al-doped hexagonal plate-shaped zinc oxide was obtained.

Comparative Example 4

A slurry was obtained by repulping 79.2 g of starting particulate zinc oxide (FINEX-50 available from Sakai Chemical Industry Co., Ltd., particle size calculated from specific surface area: 0.02 μm) with 399 ml of water. To the slurry was added 0.77 g of aluminum hydroxide hexahydrate so that the amount of aluminum was 1 mol % based on the starting zinc oxide. Separately, 601 ml of a 1.30 mol/l aqueous solution of zinc acetate was prepared. The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and aluminum hydroxide was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Al-doped hexagonal plate-shaped zinc oxide was obtained.

Comparative Example 5

A slurry was obtained by repulping 79.2 g of starting particulate zinc oxide (FINEX-50 available from Sakai Chemical Industry Co., Ltd., particle size calculated from specific surface area: 0.02 μm) with 399 ml of water. Separately, 601 ml of a 1.30 mol/l aqueous solution of zinc acetate was prepared. To the aqueous solution was added 1.89 g of soluble aluminum acetate hexahydrate so that the amount of aluminum was 1 mol % based on the starting zinc oxide. The slurry and the zinc acetate aqueous solution were added simultaneously to 200 ml of water controlled at 30° C. such that the total amounts were added over 120 minutes. Thus, a slurry mixture containing a 0.65 mol/l aqueous solution of zinc acetate, the starting particulate zinc oxide, and soluble aluminum acetate was obtained. Subsequently, the slurry mixture was heated to 95° C. over 65 minutes under stirring, and then aged at 95° C. for two hours under stirring. After the aging, the slurry mixture was immediately cooled and then filtered and washed to obtain a cake. The cake was repulped with water, heated to 95° C., stirred for two hours, filtered, washed (with water), and dried at 120° C. for 16 hours. Thus, particulate Al-doped hexagonal plate-shaped zinc oxide was obtained.

Evaluation of Properties of Particulate Zinc Oxide

The properties of the particulate zinc oxides produced in Examples 1 to 4 and Comparative Examples 1 and 3 to 5 and commercially available particulate zinc oxide used in Comparative Example 2 were measured by the following methods. The results are shown in Table 1.

Similarly to Example 1, the particulate zinc oxides produced in Examples 3 and 4 and Comparative Examples 1 and 3 to 5 were observed with a scanning electron microscope JSM-6510A (JEOL Ltd.). The resulting electron micrographs are shown in FIGS. 3 to 8.

<Particle Shape>

The particle shape was observed in a scanning electron microscope JSM-6510A (JEOL Ltd.).

<Aspect Ratio>

In the micrographs at magnifications of 2000× to 50000× taken with a scanning electron microscope JSM-6510A (JEOL Ltd.), the aspect ratio was determined as a ratio of L/T where L is an average of measured particle diameters (μm) of 100 hexagonal plate-shaped zinc oxide particles, the particle diameter being the diagonal diameter of the frontal image of the hexagonal plate-shaped surface of a hexagonal plate-shaped zinc oxide particle (the length of any one of three diagonal lines of the hexagonal plate-shaped surface of a hexagonal plate-shaped zinc oxide particle), and T is an average of measured thicknesses (μm) of 100 hexagonal plate-shaped zinc oxide particles, the thickness being the shorter length of the frontal image of the side face of a hexagonal plate-shaped zinc oxide particle (apparently rectangular particle).

<D10, D50 (Median Diameter), D90>

In the micrographs at magnifications of 2000× to 50000× taken with a scanning electron microscope JSM-6510A (JEOL Ltd.), the particle diameters (μm) of 100 hexagonal plate-shaped zinc oxide particles in the SEM image were measured. Here, the particle diameter is the diagonal diameter (the length of any one of three diagonal lines of the hexagonal plate-shaped surface of a hexagonal plate-shaped zinc oxide particle). The cumulative distribution of the particle diameters was calculated.

The particle size at which 10% by number of particles were accumulated was expressed by D10, the particle size at which 50% by number of particles were accumulated was expressed by D50, and the particle size at which 90% by number of particles were accumulated was expressed by D90.

<Brightness L Value, Redness a Value, Yellowness b Value, Whiteness W>

The brightness L value, redness a value, yellowness b value, and whiteness W were measured with a spectral colorimeter SE2000 (Nippon Denshoku Industries Co., Ltd.). A sample was put into a round-bottom cell, the cell was placed in a spectral colorimeter, and measurement was performed.

<Powder Spectral Reflectance at 1000 nm, Powder Spectral Reflectance at 1500 nm, Powder Spectral Reflectance at 2000 nm>

The powder spectral reflectance at 1000 nm, the powder spectral reflectance at 1500 nm, and the powder spectral reflectance at 2000 nm were measured with a spectrophotometer (V-570 available from JASCO Corporation). Each powder obtained in the examples and the comparative examples was put in a special cell, and the cell was placed in the spectrophotometer. The powder spectral reflectance was measured at a wavelength of 1000 nm, at a wavelength of 1500 nm, and at a wavelength of 2000 nm.

<Trivalent Metal Element Content>

The trivalent metal element content was measured with an X-ray fluorescence spectrometer ZSX Primus II (Rigaku Corporation). The measurement used the EZ scan program. The molar ratio of the trivalent metal element to the zinc element was determined using the following equation.

Trivalent metal element content based on zinc element=(Amount of trivalent metal element (mol))/(Amount of zinc element(mol)+Amount of trivalent metal element(mol))×100(%)

<Texture>

The powder texture is an indicator of slippage and roughness of powder when a small amount of a powder was placed on the skin and drawn by a finger. Each sample was evaluated on a ten-point scale (1 to 10). A higher score indicates better slippage with no roughness, and a lower score indicates poorer slippage with roughness. The powder of Comparative Example 1 was defined as a standard (score 5).

TABLE 1

| | | | Example 1 | Example 2 | Example 3 | Example 4 | Example 5 |
|---|---|---|---|---|---|---|---|
| Conditions of preparation | Starting particulate zinc oxide (material) slurry | Type of material | FINEX-50 | FINEX-50 | FINEX-50 | FINEX-50 | FINEX-50 |
| | | Particle size calculated from specific surface area (pm) of material | 0.02 | 0.02 | 0.02 | 0.02 | 0.02 |
| | | Amount of material used (g) | 79.2 | 79.6 | 78.4 | 79.2 | 80 |
| | | Amount of water for repulping of material (ml) | 399 | 399 | 399 | 399 | 399 |
| | Zinc acetate aqueous solution | Type | Zinc acetate aqueous solution | Zinc acetate aqueous solution | Zinc acetate aqueous solution | Zinc acetate aqueous solution | Zinc acetate aqueous solution |
| | | Concentration (mol/l) | 1.3 | 1.3 | 1.3 | 1.3 | 1.3 |
| | | Amount (ml) | 601 | 601 | 601 | 601 | 601 |
| | Trivalent metal chloride | Type | Aluminum chloride hexahydrate | Aluminum chloride hexahydrate | Aluminum chloride hexahydrate | Aluminum chloride hexahydrate | Gallium chloride |
| | | Amount(g) | 2.37 | 1.19 | 4.75 | 2.37 | 5.19 |
| | | Liquid to which trivalent metal chloride is to be added | Zinc acetate aqueous solution | Zinc acetate aqueous solution | Zinc acetate aqueous solution | Starting zinc oxide slurry | Zinc acetate aqueous solution |
| | | Amount of Al or Ga element (mol %) based on starting particulate zinc oxide | 1 | 0.5 | 2 | 1 | 3 |
| | | Mixing time (min) | 120 | 120 | 120 | 120 | 120 |
| | | Mixing temperature (° C.) | 30 | 30 | 30 | 30 | 30 |
| | | Concentration of zinc acetate in aqueous solution (moVl) after mixing | 0.65 | 0.65 | 0.65 | 0.65 | 0.65 |
| | | Aging temperature (° C.) | 95 | 95 | 95 | 95 | 95 |
| | | Aging time (Hr) | 2 | 2 | 2 | 2 | 2 |
| Properties of particle | | Composition of obtained particle | Zinc oxide | Zinc oxide | Zinc oxide | Zinc oxide | Zinc oxide |
| | | Shape of obtained particle | Hexagonal plate shape | Hexagonal plate shape | Hexagonal plate shape | Hexagonal plate shape | Hexagonal plate shape |
| | | Aspect ratio | 5.3 | 5.2 | 5.2 | 5.3 | 16.7 |
| | | Aluminum or gallium element content (mol%) based on zinc element | 0.34 | 0.16 | 0.94 | 0.47 | 0.94 |
| | | D10 (μm) | 0.50 | 0.48 | 0.47 | 0.53 | 0.94 |
| | | Median diameter D50 (μm) | 0.71 | 0.78 | 0.79 | 0.78 | 1.24 |
| | | D90 (μm) | 0.87 | 1.00 | 0.95 | 1.01 | 1.53 |
| | | D90/D10 | 1.7 | 2.1 | 2.0 | 1.9 | 1.6 |
| | | Brightness L value | 94.03 | 94.23 | 90.26 | 92.23 | 94.15 |
| | | Redness a value | −1.38 | −1.27 | −1.20 | −1.33 | −2.03 |
| | | Yellowness b value | 1.73 | 1.61 | 0.84 | 1.26 | 2.12 |
| | | Whiteness W | 93.64 | 93.88 | 90.15 | 92.02 | 93.45 |
| | | Powder spectral reflectance (%) at 1000 nm | 82.78 | 82.49 | 81.74 | 82.60 | 82.24 |
| | | Powder spectral reflectance (%) at 1500 nm | 74.15 | 75.70 | 74.12 | 75.95 | 71.03 |
| | | Powder spectral reflectance (%) at 2000 nm | 62.66 | 65.90 | 62.63 | 66.40 | 53.99 |
| | | Texture | 8 | 8 | 8 | 8 | 9 |

| | | | Comparative Example 1 | Comparative Example 2 | Comparative Example 3 | Comparative Example 4 | Comparative Example 5 |
|---|---|---|---|---|---|---|---|
| Conditions of preparation | Starting particulate zinc oxide (material) slurry | Type of material | FINEX-50 | | FINEX-50 | FINEX-50 | FINEX-50 |
| | | Particle size calculated from specific surface area (pm) of material | 0.02 | | 0.02 | 0.02 | 0.02 |
| | | Amount of material used (g) | 80 | | 79.2 | 79.2 | 79.2 |
| | | Amount of water for repulping of material (ml) | 399 | | 399 | 399 | 399 |
| | Zinc acetate aqueous solution | Type | Zinc acetate aqueous solution | | Zinc acetate aqueous solution | Zinc acetate aqueous solution | Zinc acetate aqueous solution |
| | | Concentration (mol/l) | 1.3 | | 1.3 | 1.3 | 1.3 |
| | | Amount (ml) | 601 | | 601 | 601 | 601 |

TABLE 1-continued

| | | | | | Aluminum sulfate | Aluminum hydroxide | Soluble aluminum acetate |
|---|---|---|---|---|---|---|---|
| | Trivalent metal chloride | Type | | | | | |
| | | Amount(g) | | | 3.30 | 0.77 | 1.89 |
| | | Liquid to which trivalent metal chloride is to be added | | | Zinc acetate aqueous solution | Starting zinc oxide slurry | Zinc acetate aqueous solution |
| | | Amount of Al or Ga element (mol %) based on starting particulate zinc oxide | | | 1 | 1 | 1 |
| | | Mixing time (min) | 120 | | 120 | 120 | 120 |
| | | Mixing temperature (° C.) | 30 | | 30 | 30 | 30 |
| | | Concentration of zinc acetate in aqueous solution (moVl) after mixing | 0.65 | | 0.65 | 0.65 | 0.65 |
| | | Aging temperature (° C.) | 95 | | 95 | 95 | 95 |
| | | Aging time (Hr) | 2 | | 2 | 2 | 2 |
| Properties of particle | | Composition of obtained particle | Zinc oxide | Zinc oxide | Zinc oxide | Zinc oxide | Zinc oxide |
| | | Shape of obtained particle | Hexagonal plate shape | Amorphous | Hexagonal plate shape | Hexagonal plate shape | Hexagonal plate shape |
| | | Aspect ratio | 2.8 | | 3.8 | 3.6 | 3.6 |
| | | Aluminum or gallium element content (mol%) based on zinc element | 0 | 0.73 | 0.60 | 0.47 | 0.20 |
| | | D10 (μm) | 0.33 | 0.07 | 0.33 | 0.47 | 0.38 |
| | | Median diameter D50 (μm) | 0.64 | 0.10 | 0.50 | 0.69 | 0.59 |
| | | D90 (μm) | 0.99 | 0.16 | 0.70 | 0.91 | 0.81 |
| | | D90/D10 | 3.0 | 2.2 | 2.1 | 1.9 | 2.1 |
| | | Brightness L value | 96.82 | 86.17 | 95.52 | 95.06 | 95.21 |
| | | Redness a value | −0.86 | −2.17 | −0.98 | −0.85 | −0.84 |
| | | Yellowness b value | 1.78 | 0.90 | 1.69 | 1.90 | 1.22 |
| | | Whiteness W | 96.25 | 85.97 | 95.11 | 94.64 | 94.99 |
| | | Powder spectral reflectance (%) at 1000 nm | 86.31 | 54.12 | 87.21 | 89.16 | 87.99 |
| | | Powder spectral reflectance (%) at 1500 nm | 82.64 | 19.11 | 83.32 | 84.21 | 84.63 |
| | | Powder spectral reflectance (%) at 2000 nm | 78.88 | 7.49 | 76.33 | 78.51 | 79.13 |
| | | Texture | 5 | 2 | 6 | 6 | 6 |

Table 1 demonstrates that the method for producing trivalent metal-doped hexagonal plate-shaped zinc oxide of the present invention can produce trivalent metal-doped hexagonal plate-shaped zinc oxide having excellent infrared blocking ability, high whiteness, and excellent texture during use owing to the high aspect ratio.

The invention claimed is:

1. Trivalent metal-doped hexagonal plate-shaped zinc oxide, having an aspect ratio of 2.5 or greater, the trivalent metal-doped hexagonal plate-shaped zinc oxide having a trivalent metal element content based on a zinc element of 0.15 to 5 mol %, a whiteness of 90 or higher, and a powder spectral reflectance at a wavelength of 1500 nm of 80% or less.

2. The trivalent metal-doped hexagonal plate-shaped zinc oxide according to claim 1, wherein the trivalent metal is at least one selected from the group consisting of aluminum, gallium, and indium.

3. The trivalent metal-doped hexagonal plate-shaped zinc oxide according to claim 1, wherein the trivalent metal-doped hexagonal plate-shaped zinc oxide has a median size of 0.05 to 5 μm.

4. The trivalent metal-doped hexagonal plate-shaped zinc oxide according to claim 1, wherein the trivalent metal-doped hexagonal plate-shaped zinc oxide has a median diameter of 0.08 to 5 μm.

5. The trivalent metal-doped hexagonal plate-shaped zinc oxide according to claim 1, wherein the trivalent metal-doped hexagonal plate-shaped zinc oxide has a median diameter of 0.71 to 5 μm.

6. The trivalent metal-doped hexagonal plate-shaped zinc oxide according to claim 1, wherein the trivalent metal-doped hexagonal plate-shaped zinc oxide has a ratio D90/D10 of 2.5 or less.

7. The trivalent metal-doped hexagonal plate-shaped zinc oxide according to claim 1, wherein the aspect ratio is determined by using a scanning electron microscope that produces micrographs at 2000× to 50,000× magnifications, and the aspect ratio is determined as a ratio of L/T, wherein L is an average of measured particle diameters of 100 hexagonal plate-shaped zinc oxide particles, each of the particle diameters being a diagonal diameter of a frontal image of a hexagonal plate-shaped surface of a hexagonal plate-shaped zinc oxide particle, and T is an average of measured thicknesses of the 100 hexagonal plate-shaped zinc oxide particles, each of the thicknesses being a shorter length of the frontal image of a side face of the hexagonal plate-shaped zinc oxide particle.

* * * * *